(12) United States Patent
Gunawan

(10) Patent No.: US 11,297,867 B2
(45) Date of Patent: Apr. 12, 2022

(54) FUNCTIONAL FOOD AND THEIR MANUFACTURING PROCESS AS WELL AS THE APPLICATION ON FOOD AND BEVERAGE PRODUCTS

(71) Applicant: PT. Lautan Natural Krimerindo, Mojokerto (ID)

(72) Inventor: Hendrik Gunawan, Surabaya (ID)

(73) Assignee: PT. Lautan Natural Krimerindo, Mojokerto (ID)

( * ) Notice: Subject to any disclaimer, the term of this patent is extended or adjusted under 35 U.S.C. 154(b) by 0 days.

(21) Appl. No.: 15/614,633

(22) Filed: Jun. 6, 2017

(65) Prior Publication Data

US 2018/0027861 A1 Feb. 1, 2018

(30) Foreign Application Priority Data

Jul. 26, 2016 (ID) .............................. P00201604931

(51) Int. Cl.
| | |
|---|---|
| *A23L 33/135* | (2016.01) |
| *A23L 33/00* | (2016.01) |
| *A23C 11/08* | (2006.01) |
| *A23L 11/50* | (2021.01) |
| *A23K 10/18* | (2016.01) |
| *A23L 33/17* | (2016.01) |
| *A23L 33/115* | (2016.01) |
| *A23L 33/125* | (2016.01) |
| *A23C 11/10* | (2021.01) |
| *C12N 1/20* | (2006.01) |

(52) U.S. Cl.
CPC ............ *A23L 33/135* (2016.08); *A23C 11/08* (2013.01); *A23C 11/106* (2013.01); *A23K 10/18* (2016.05); *A23L 11/50* (2021.01); *A23L 33/115* (2016.08); *A23L 33/125* (2016.08); *A23L 33/17* (2016.08); *A23L 33/40* (2016.08); *C12N 1/20* (2013.01)

(58) Field of Classification Search
CPC ........ A23L 33/17; A23L 33/115; A23L 11/50; A23L 33/135; A23L 11/08; A23L 11/106; A23L 33/40; A23L 33/125; A23K 10/18; C12N 1/20
USPC .......................................... 426/72, 588, 658
See application file for complete search history.

(56) References Cited

U.S. PATENT DOCUMENTS

| | | | |
|---|---|---|---|
| 4,046,926 A * | 9/1977 | Gardiner ................ | A23C 11/08 426/613 |
| 5,284,674 A * | 2/1994 | Fazio ..................... | A23C 11/04 426/580 |
| 6,322,843 B1 * | 11/2001 | Schuurman ............ | A23D 7/001 426/602 |
| 6,375,994 B1 * | 4/2002 | Paul ....................... | A61K 9/205 424/489 |
| 6,426,110 B1 * | 7/2002 | Basa ...................... | A23C 11/06 426/588 |
| 6,673,384 B1 * | 1/2004 | Villagran ................ | A23G 1/56 426/575 |
| 2003/0068429 A1 * | 4/2003 | Frippiat ................ | A61K 31/733 426/658 |
| 2004/0060265 A1 * | 4/2004 | Boeckle .................. | B65B 1/08 53/476 |
| 2005/0208179 A1 * | 9/2005 | Albrecht .................. | A23L 2/39 426/72 |
| 2006/0088574 A1 * | 4/2006 | Manning ................. | A23L 33/40 424/439 |
| 2010/0316762 A1 * | 12/2010 | Nakaya .................. | A21D 8/042 426/18 |
| 2012/0034366 A1 * | 2/2012 | Hoffman ................ | A23L 29/30 426/548 |
| 2012/0121776 A1 * | 5/2012 | Arnaudov ............... | A23G 9/38 426/329 |
| 2013/0202771 A1 * | 8/2013 | Corbin ................ | A23D 7/0056 426/603 |

OTHER PUBLICATIONS

NPL Prabhakaran, (From Advances in Pharmacology, 2010: Under Oil Palm (*Elaeis guineensis* Jacquin, K.P. Prabhakaran Nair, in Agronomy and Economy of Important Tree Crops of the Developin p. 1, in 2010 ( https://www.sciencedirect.com/topics/agricultural-and-biological-sciences/lauric-acid).*

* cited by examiner

*Primary Examiner* — Erik Kashnikow
*Assistant Examiner* — Bhaskar Mukhopadhyay
(74) *Attorney, Agent, or Firm* — Bayramoglu Law Offices LLC

(57) ABSTRACT

A functional food in the form of agglomeration powder which has the characteristics of easily soluble in water. Functional food product in accordance with the present invention contains carbohydrates of oligosaccharides component rich of food-fiber, and also serves as prebiotic. The advantages of this functional food are sugar free, Trans Fat free, and lactose-free. Moreover, it can be widely applied both in the food and beverages so that to facilitate consumers in consuming to the products.

7 Claims, 1 Drawing Sheet

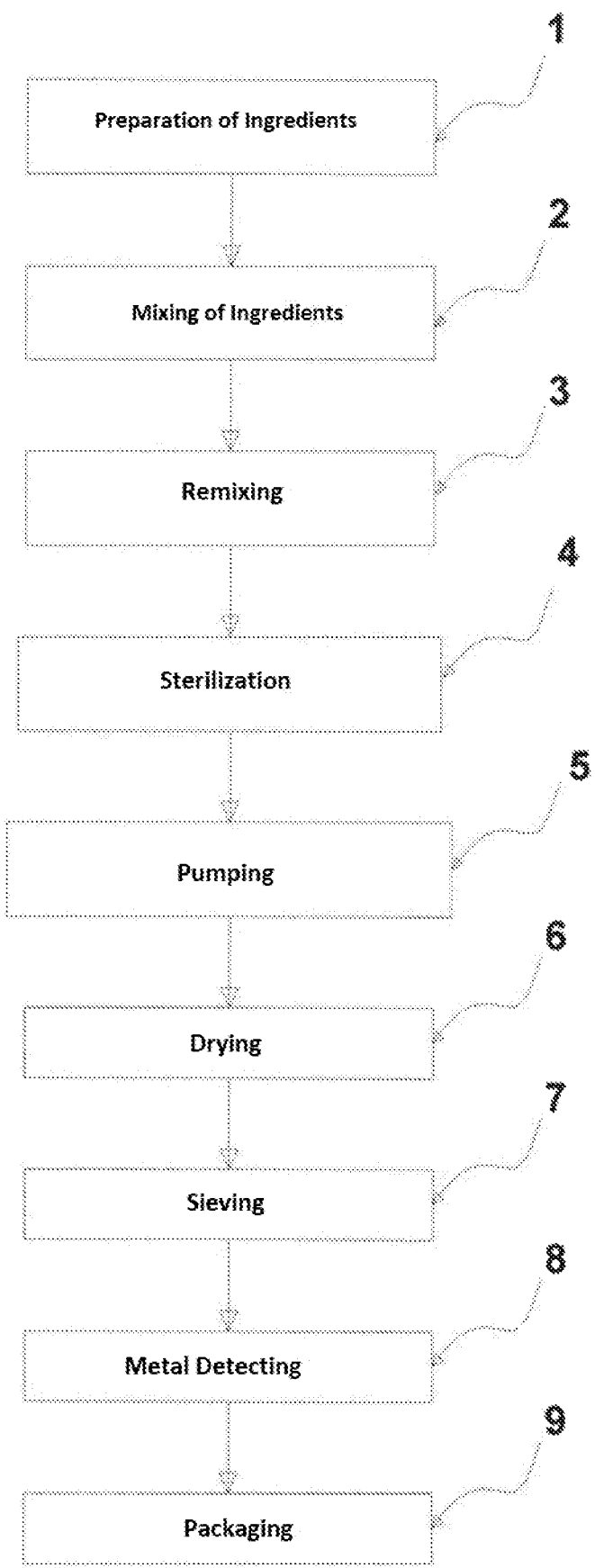

FUNCTIONAL FOOD AND THEIR MANUFACTURING PROCESS AS WELL AS THE APPLICATION ON FOOD AND BEVERAGE PRODUCTS

CROSS REFERENCE TO RELATED APPLICATIONS

This application is based upon and claims priority to Indonesian Patent Application No. P00201604931 filed on Jul. 26, 2016, the entire contents of which are incorporated herein by reference.

TECHNICAL FIELD

This invention relates generally to functional food, and more specifically this invention relates to the powder functional food containing carbohydrate of oligosaccharide component rich of dietary fiber which also serves as a prebiotic. Whereby in this invention, it is generated powder functional food product with some advantages, such as sugar free, Trans Fat free and lactose-free. The products of the invention can be applied widely both in food and beverages.

BACKGROUND OF THE INVENTION

Currently, various health problems come up due to excessive food consumption and inappropriate dietary pattern. One of the health problems due to excessive food consumption is in the form of increased blood sugar levels beyond normal limits. Short-term effects caused by high levels of sugar in the blood that the patient would be easy to feel weak, fatigue and sleepy while doing everyday activities. Subsequent impact could be that of frequent urination that may lead to dehydration and followed by weight loss. While the long-term effect caused by high levels of sugar in the blood is that there will be impaired pancreatic function in which the pancreas is to secrete the insulin hormone. The insulin hormone plays a role in maintaining blood sugar levels. So that if the pancreas is disturbed then it will lead to high blood sugar levels, which in the world of health known as diabetes mellitus.

Other long-term impact by high levels of sugar in the blood is the immune system disorders so that patients are susceptible to infections such as influenza. The next impact is that the nervous system damage in the form of peripheral neuropathy in which the nerves in the hands and feet are damaged so that the patient will experience tingling in the hands and feet. If the blood sugar levels stay high over many years, it can cause visual impairment due to damaged retina. The symptoms include dark spots, unfocused vision, blurred vision and may eventually lead to blindness.

Extended high blood sugar levels for many years may also cause arteriosclerosis, in which there is a hardening of the arteries being the blood vessels supplier of blood to various organs including the heart and brain. Blood with high sugar content will cause the arteries to lose flexibility so that it becomes hard. Besides, the arterial wall will be thicker because of the buildup of excessive sugar so that the arteries narrowed. Subsequent impact of high blood sugar levels is impaired kidney function, in which the kidneys function is to filter out toxins and impurities in the blood. If the sugar content is high, the workload of the kidneys become severe that the kidneys have to work harder, which in turn will damage the kidneys.

The next health problems due to improper food consumption patterns is the impact on people with lactose intolerance. Whereby lactose intolerance is usually hereditary i.e. if parents have lactose intolerance then their children will also tend to have lactose intolerance. Lactose is a disaccharide form of carbohydrates that can be broken down into simpler form, namely galactose and glucose. The content of lactose is mainly found in milk in which the lactose content is 2 to 8 percent of the total weight of the milk. Health problems that often arise in people with lactose intolerance are stomach cramps, nausea, bloating and diarrhea. So that people with lactose intolerance are advised to avoid the consumption of foods containing dairy.

In line with consumer understanding of the influence of food on health, the consumer demand for food to consume no longer just have to have a good nutritional composition, or good appearance and interesting taste. But today, the consumer requires that the food must also have specific physiological functions that are beneficial to health. This demand led to the current functional food grows and develops rapidly. The definition of functional foods according to BPOM 2005 is processed food containing one or more functional components which based on scientific studies have certain physiological functions, proved to be harmless and beneficial to health.

With so many various health problems due to excessive dietary pattern and improper diet and increasing consumer demand for functional foods, the inventors have made a breakthrough by producing functional food products. Whereby the functional foods in accordance with the present invention have the advantages in the form of sugar free, Trans Fat free, and lactose-free and can be applied to both food products and beverage products.

SUMMARY OF THE INVENTION

As described above, this invention relates generally to functional food, and more specifically the present invention relates to powder functional food containing carbohydrate of oligosaccharide component rich of dietary fiber which also serves as prebiotic. The products of the present invention can be applied widely both in food and beverages.

The main objective of the present invention is to produce a functional food product containing carbohydrates from oligosaccharides component rich of food fiber and also function as a prebiotic. In this invention, oligosaccharides which is used for the manufacture of functional food product has a glucose level <1.5%. The excellences of functional food products according to this invention are sugar free, Trans Fat free, and lactose-free. Another advantage is that it can help smooth the process of digestion in the gut, because the functional food product according to this invention will become food for useful bacteria (probiotics) that live in the human colon.

A further objective of the invention is to produce functional food products which can be a new choice for consumers. Whereby the presence of functional food products in accordance with the invention, the consumers concerned with health can take advantages of these products to improve diet. By consuming functional food products in accordance with the present invention regularly, it will reduce a wide range of health problems related to diet. In this case the functional food product may be a product that is safe for consumption by people with diabetes and lactose intolerance.

Another objective of the present invention is to give consumers convenience in consuming functional food products. Whereby in the present invention, functional food product can be applied in various food and beverage products. This is because there are some consumers who feel comfortable when consuming a functional food product in the form of food. But there are some other consumers who feel comfortable when consuming functional food product in the form of drinks. Thus, consumers can decide for themselves how to take functional foods according to their wish.

Functional food product in accordance with the present invention is in the form of agglomeration powder that has the characteristics of easily soluble in water and consist of carbohydrates that are rich of dietary fiber, fat, protein, emulsifier, stabilizers and Free Flowing Agent. The functional food product contains oligosaccharides and carbohydrate components that also serves as prebiotic. In the invention, oligosaccharides used for the manufacture of functional food product has a glucose level <1.5%. The advantages of this functional food product are that it can help lower the risk of diabetes mellitus. Moreover, it can help improve the smoothness of the process of digestion in the gut.

BRIEF DESCRIPTION OF THE DRAWINGS

FIG. 1 is the stage of producing functional foods in accordance with the present invention.

DETAILED DESCRIPTION OF THE INVENTION

As described previously, the definition of functional foods is in accordance with BPOM 2005, namely processed food containing one or more functional components which based on scientific studies have certain physiological functions, proved to be harmless and beneficial to health. In order to be categorized as functional food, the food must be consumed as befits a food or beverage with sensory characteristics such as appearance, color, texture and flavor that can be accepted by the consumer and does not provide contraindications and side effects on the metabolism of other nutrients. Although it has health benefits, functional foods are not drugs or dietary supplements. While drug is used to treat a disease, functional food is intended more to decrease the risk, slowing or prevention of certain diseases. The main objective is to prevent degenerative diseases and increase endurance, especially in the post-hospital recovery process.

Functional food products contain carbohydrates from oligosaccharides component rich of food-fiber, and also serves as prebiotic. Carbohydrates are sources of energy for human life activity in addition to protein and fat. Carbohydrates are known in various forms that have different chemical compounds, among others: monosaccharide, disaccharide, oligosaccharides and polysaccharides. Oligosaccharide is a combination of monosaccharide molecules contain between 2 (two) to 8 (eight) monosaccharide molecules. So that oligosaccharides can be a disaccharide, trisaccharide and others.

While prebiotics are food for useful bacteria (probiotics) that live in the human colon. In order to be a prebiotic, a food should not be hydrolysed or absorbed in the upper part of the gastrointestinal tract so that food can get to the large intestine to be consumed by probiotic bacteria. Until now, the prebiotic sources that have been produced commercially are of the types of oligosaccharides such as Isomalto oligosaccharides (IMO), Fructo oligosaccharides (FOS) and Galacto oligosaccharides (GOS). Thus functional foods will help improve the smoothness of the process of digestion in the gut.

The ingredients for the manufacture of Functional Food include:

1. Carbohydrates

Carbohydrate sources used is in the form oligosaccharides include Fructo oligosaccharides, Isomalto oligosaccharides and galacto oligosaccharides or the combination of such sources. The carbohydrate level in these functional foods is 40 wt % to 80 wt % with high levels of dietary fiber of 90 wt % to 95 wt % (of total carbohydrates) and has a monosaccharide level below 1.5 wt %.

2. Fats

The source of fat is derived from non-hydrogenated coconut oil, non-hydrogenated palm oil, fully hydrogenated coconut oil, fully hydrogenated palm kernel oil, coconut oil interesterification, palm kernel oil interesterification or the blending of these oils. The level of fat in functional foods is 20 wt % to 60 wt %, while the trans fat content in the source of fat is less than 0.5 wt %.

3. Protein

Sources of protein are derived from the lactose-free milk protein namely casein and sodium caseinate or the mixing of the sources. The level of protein in the functional food is 1 wt % to 110 wt %.

4. Emulsifier

Emulsifier used comes from Mono and diglycerides of fatty acids, diacetyl tartaric acid ester of mono- and diglycerides (DATEM) and sodium stearoyl lactylate (SSL) or the mixing of the sources. The content of emulsifier in this functional food is 1 wt % to 2 wt %.

5. Stabilizer

The stabilizer is derived from dikalium phosphates, sodium polyphosphates, trisodium citrate or the mixing of the sources. The content of stabilizers in this functional food is 2 wt % to 3 wt %.

6. Free Flowing Agent

Free Flowing Agent is derived from silicon dioxide and alumina silicate, with the use of 0.5 wt % to 1 wt %.

7. Water

The water required is calculated with a target total solid mix of carbohydrates, fats, proteins, emulsifiers and stabilizers by adding water until the total solid is 60% to 72%.

The process of making functional food according to the present invention can be seen in FIG. 1, in which it shows the stage of making functional foods. These stages include:

1. Preparation of ingredients (1)

This process is the preparation of ingredients that include carbohydrates, fats, proteins, emulsifiers, stabilizers, Free Flowing Agent and water with a composition as described above.

2. Mixing the ingredients (2)

This is the process of mixing carbohydrates, fats, proteins, emulsifiers, stabilizers and water. The process of mixing the ingredients (2) uses homomixer so that giving emulsion with a solid total of 60% to 72%.

3. Remixing (3)

Remixing process (3) is done in order to produce a more uniformly emulsion mixture by passing them through homogenizer pressure. This process is taking place in two phases with total pressure of 150 to 250 bar.

4. Sterilization (4)

The process of sterilization (4) is done to kill microbes that can harm the body. The process of sterilization (4) is done by passing a mixture of emulsion in the form of pasteurization unit heat exchanger with a temperature of 75 to 95 degrees Celsius and held for at least 30 seconds.

5. Pumping (5)

The process of pumping (5) aims to remove the emulsion that has been sterilized from pasteurization units to the drying units. The process of pumping (5) is done using high pressure pump units.

6. Drying (6)

The process of drying (6) aims to reduce drastically the water content in order to obtain the final product in the form of powder. The drying process (6) is done using a spray dryer unit with inlet air temperature of 150 to 200 Celsius degrees and the discharge air temperature is 88 to 95 Celsius degrees. During the drying process (6) the moisture content of the product is maintained at 1.5 wt % to 5.0 wt %.

7. Sieving (7)

The process of sieving (7) aims to produce a final product namely a powder with a uniform grain, in which the sieving process (7) is done using shifter units. During the sieving process (7) Free flowing Agent is added so that the final product is not easily agglomerating.

8. Metal Detecting (8)

The process of checking the metal content (8) aims to ensure the final product is free of metal content so it is safe for consumption. The process of checking the metal content (8) is done using metal detecting.

9. Packaging (9)

The packaging process (9) aims to keep the final product from being exposed to the outside air that may raise the level of water, so that the product will be more durable in the storage. The packaging process (9) is done using a packaging machine in which the final product is powder wrapped into the packaging with weight as needed.

The process of making functional foods in accordance with the present invention is done using equipment that meet the standards of the food industry. Surely the instruments relating to the control of parameters of temperature, pressure and processing time should be monitored and calibrated periodically to ensure the accuracy of the instrument. So that the process of making functional foods will ensure the quality of the products in good quality and meet food safety requirements. Thus, consumers would feel confident to consume functional food product and get the advantage of increasing the quality of their health.

In addition to having functional properties that are good for health as described above, functional food according to the present invention also has another advantage in terms of organoleptic namely taste. Whereby the functional food has a sweet, creamy and thick mouthfeel taste. In general, functional food in accordance with the present invention can be consumed directly with or without the addition of other ingredients. Functional food can be consumed directly by dissolving 10 grams of powder functional food into 100 mL of hot water with a temperature of 85±5° C. In addition to direct consumption, functional foods can be added to drinks or food processed products. The example in drinks such as coffee and tea:

a. Application in coffee in one serving: coffee 1.75 grams (1 teaspoon), functional food 12 grams (3 teaspoons) and hot water 85±5° C. 120 mL. Ways of making: Coffee and functional foods are put into a cup and add hot water 85±5° C. 120 ml and stir until completely dissolved.

b. Application in tea in one serving: teabag 1 bag, functional food 12 grams (3 teaspoons) and hot water 85±5° C. 120 mL. Ways of making: 1 bag of teabag is brewed with hot water 85±5° C. 120 mL cup for 3-5 minutes. Add functional food 12 grams (3 teaspoons) and stir until completely dissolved.

The benefits in each serving (1 cup) is high in fiber (over 6 grams per 100 grams of ingredients), sugar free (less than <0.5 grams per 100 grams of ingredients), lactose-free so it is safe for people with lactose intolerance, fat/Trans oil-free and no cholesterol.

Application of functional food in processed foods is for example for making pancakes, wherein the functional food according to the present invention can be used to substitute the milk so it is suitable for people with lactose intolerance. The application in the making of pancakes is: 100 grams of wheat flour, 2 grams of baking powder, 1.5 grams of salt, 30 grams of non-caloric sugar, 0.2 grams of vanilla, 13.8 grams of functional food, 55 grams of eggs, 17 grams of unsalted butter and 100 grams of water. Way of making pancakes is as follows:

a. Weigh the dry ingredients such as flour, baking powder, salt, non-caloric sugar, vanilla, stir until blended (I)

b. Melt the unsalted butter and refrigerate (II)

c. Dissolve functional food in hot water until dissolved (III)

d. Shake the eggs, put in (II) and shake until evenly distributed, put in (II) and shake until evenly distributed.

e. Put in the dry ingredients (I) slowly while stirring until evenly distributed.

f. Heat the frying pan over medium heat.

g. Pour the batter (±40 grams) in the frying pan for ±2 minutes, then turn and heat the other side until done.

The advantages in each serving (45 grams) are high in fiber (over 6 grams per 100 grams of ingredients), sugar free (less than <0.5 grams per 100 grams of ingredients), lactose-free so it is safe for people with lactose intolerance. It can also be added with sugar, but it is advised not to do so as functional food generally has a sweet taste. Moreover without the addition of sugars, better benefits are gained for people with diabetes, as well as good for a low-calorie diet.

The explanation and description which refer to the FIGURES in the description are intended only for illustrative purposes only, and does not constitute restrictions on the invention, since modifications can be made without departing from the claimed patent protection in the present invention.

What is claimed is:

1. A functional food in the form of an agglomeration powder containing dietary fiber comprising:

a carbohydrate content of 51 wt % to 63 wt %; wherein the carbohydrate comprises the dietary fiber content in a range of 90 wt % to 95 wt % and a monosaccharide content of less than 1.5 wt % and the carbohydrate is one or more selected from the group consisting of Fructo oligosaccharides, Isomalto oligosaccharides and galacto oligosaccharide;

a fat content of 25 wt % to 54 wt %;

a protein content of 1 wt % to 5 wt %;

an emulsifier content of 1 wt % to 2 wt %;

a stabilizer content of 2 wt % to 3 wt %; and a free flowing agent content of 0.5 wt % to 1 wt %; and a moisture content of 1.5 wt % to 5.0 wt %.

2. The functional food according to claim 1, wherein the fat is one or more selected from the group consisting of non-hydrogenated coconut oil, non-hydrogenated palm oil, fully hydrogenated coconut oil, fully hydrogenated palm kernel oil, coconut oil interesterification, and palm kernel oil interesterification.

3. The functional food according to claim 1, wherein the protein is lactose-free milk proteins.

4. The functional food according to claim 1, wherein the emulsifier is one or more selected from the group consisting of Mono and diglycerides of fatty acids, fatty acid esters, diacetyl tartaric acid ester of mono- and diglycerides (DATEM) and sodium stearoyl lactylate (SSL).

5. The functional food according to claim 1, wherein the stabilizer is one or more selected from the group consisting of dipotassium phosphates, sodium polyphosphate, and tri-sodium citrate.

6. The functional food according to claim 1, wherein the free flowing agent content is a silicon dioxide or an alumina silicates.

7. The functional food according to claim 3, wherein the lactose-free milk proteins are casein and sodium caseinate.

* * * * *